United States Patent [19]

Geier

[11] Patent Number: 4,845,125

[45] Date of Patent: Jul. 4, 1989

[54] CHEMOLYTIC EDTA-CITRIC ACID COMPOSITION FOR DISSOLUTION OF CALCULI

[75] Inventor: George E. Geier, Indianapolis, Ind.

[73] Assignee: Indianapolis Center for Advanced Research, Inc., Indianapolis, Ind.

[21] Appl. No.: 119,037

[22] Filed: Nov. 10, 1987

[51] Int. Cl.$^4$ .................. A61K 9/08; A61K 31/19; A61K 31/195; A61K 31/205

[52] U.S. Cl. ........................ 514/561; 252/DIG. 11; 514/557; 514/566; 514/836; 514/891; 128/24 A; 128/328

[58] Field of Search ............... 514/557, 891, 566, 561, 514/836; 134/22.14; 252/82, 87, 142, 148, DIG. 11; 128/24 A, 328

[56] References Cited

U.S. PATENT DOCUMENTS

| | | | |
|---|---|---|---|
| 3,184,381 | 5/1965 | Ashmead | 167/53 |
| 3,328,304 | 6/1967 | Globus | 252/80 |
| 3,492,238 | 1/1970 | Wohlberg | 252/87 |
| 3,838,196 | 9/1974 | Mercer | 424/319 |
| 4,276,185 | 6/1981 | Martin | 252/87 |
| 4,637,899 | 1/1987 | Kennedy | 252/542 |
| 4,682,600 | 7/1987 | Haas | 128/328 |
| 4,708,805 | 11/1987 | D'Muhala | 210/698 |

FOREIGN PATENT DOCUMENTS

| | | | |
|---|---|---|---|
| 3046580 | 7/1982 | Fed. Rep. of Germany. | |
| 0197624 | 10/1985 | Japan. | |
| 2127484 | 6/1987 | Japan | 252/82 |

OTHER PUBLICATIONS

Chemical Abstracts, No. 800g, vol. 91, No. 1, "Endogenous Excretion of Calcium: Effects of Sodium Oxalate, Sodium Citrate, Sodium Lactate and EDTA", 1978.
"Experimental Observations on Dissolution of Uric Acid Calculi", Sadi, M. V. et al., *The Journal of Urology*, vol. 134, Sep. 1985, pp. 575–579.
"Percutaneous Catheter Dissolution of Cystine Calculi", Dretler, Pfister, Newhouse and Prien, Jr., *The Journal of Urology*, vol. 131, Feb. 1984, pp. 216–219.
"Dissolution of Urinary Stones by Calcium–Chelating Agents—A Study Using a Model System", F. Ziolkowski and D. Perrin, *Investigative Urology*, vol. 15, No. 3, Nov. 1977, pp. 208–211.
"Dissolution of Renal Calculi with Dicloxacillin", Lewis, G. A., Schuster, G. A., Cooper, R. A., *Urology*, Oct. 1983, vol. XXII, No. 4, pp. 401–403.
"Adjunctive Chemotherapy of Infection–Induced Staghorn Calculi", Griffith, D. P., Moskowitz, P. A., Carlton, Jr., C. E., *The Journal of Urology*, vol. 121, Jun. 1979, pp. 711–715.
"Hemiacidrin Renal Irrigation: Complications and Successful Management", Klein, R. S., Cattolica, E. V., Rankin, K. N., *The Journal of Urology*, vol. 128, Aug. 1982, pp. 241–242.
"Primary Dissolution Therapy of Struvite Calculi", Dretler, S. P., Pfister, R. C., *Journal of Urology*, vol. 131, May, 1984, pp. 861–863.
"Hemiacidrin Irrigation in the Management of Struvite Calculi: Long-Term Results", *The Journal of Urology*, vol. 130, Dec. 1983, Sant, G. R., Blaivas, J. G., Meares, Jr., E. M., pp. 1048–1050.
"Percutaneous Dissolution of Renal Calculi", Dretler, S. P., Pfister, R. C., *Ann. Rev. Med.*, 1983, 34:359–66.
"Dissolution of Residual Renal Calculi with Hemiacidrin", Jacobs, S. C., Gittes, R. F., *The Journal of Urology*, vol. 115, Jan. 1976, pp. 2–4.
"Outpatient Irrigation of the Renal Collecting System with 10 Per Cent Hemiacidrin: Cumulative Experience of 365 Days in 13 Patients", Palmer, J. M., Bishai, M. B., Mallon, D. S., *The Journal of Urology*, vol. 138, Aug. 1987, pp. 262–265.

*Primary Examiner*—Dennis Albrecht
*Assistant Examiner*—Kathlene Markowski
*Attorney, Agent, or Firm*—Barnes & Thornburg

[57] ABSTRACT

An improved composition for dissolution of renal calculi is disclosed. The composition includes citric acid, preferably at about 10 to about 15% by weight, and an effective amount of a pharmacologically acceptable chelating agent such as EDTA in a sterile aqueous solution having a pH between about 3 and about 4.5. In vivo irrigation with the improved formulation, optionally in combination with incident ultrasound therapy promotes rapid stone dissolution with minimal complications for the patient.

13 Claims, 1 Drawing Sheet

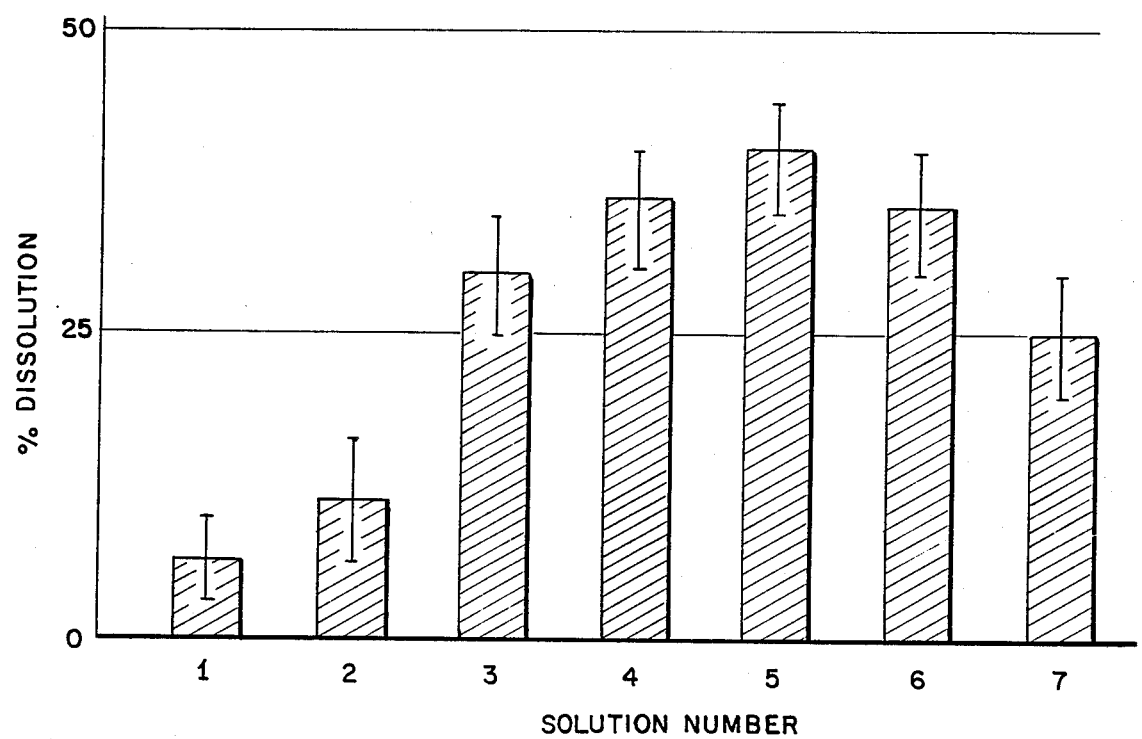

CHEMOLYTIC EDTA-CITRIC ACID COMPOSITION FOR DISSOLUTION OF CALCULI

BACKGROUND AND SUMMARY OF THE INVENTION

This invention relates to a composition and process for the treatment of patients afflicted with renal calculi (kidney stones). More particularly, this invention is directed to a sterile solution adapted for in vivo dissolution of struvite kidney stones.

Renal calculi represent a difficult therapeutic challenge. Even with the dramatic changes which have occurred in the management of upper urinary tract calculi with the introduction of extracorporeal shock wave lithotripsy (ESWL) and the popularization of percutaneous nephrostolithotomy (PCNL), patients receiving treatment by such procedures still are known to retain stone fragments which can lead to new kidney stone growth. To help clear the upper urinary tract of such potentially troublesome fragments, there has been renewed interest in chemolysis, that is the chemical dissolution of kidney stones in vivo with sterile chemolytic solutions.

Historically, chemolysis of renal calculi is one of the oldest forms of kidney stone therapy. Early chemolysis by citrate based compositions initially suggested great promise using retrograde catheters, but results obtained were found to be not comparable with surgical techniques. Calculi recurrence rates were high and consequently interest in that method of treatment declined. The initially developed chemolytic formulation and later modifications thereof still enjoyed limited applicability because of required long hospitalization and toxic side effects. While a few new chemolytic agents have been proposed over the past twenty years, only one composition, hemiacidrin, sold by the Guardian Chemical Company under the name Renacidin ®, has enjoyed significant medical use. The Renacidin ® brand composition is a sterile aqueous solution containing 4% citric acid, 1% D-gluconic acid buffered with sodium carbonate and magnesium carbonate. Hemiacidrin thus comprises citric acid and D-gluconic acid in a 4 to 1 weight ratio with buffering amounts of sodium carbonate and magnesium carbonate. Routinely, hemiacidrin is utilized at concentrations from about 2.5% to about 15% in sterile aqueous solutions for clinical use following percutaneous stone procedures for irrigation of the remaining small fragments. A 5% hemiacidrin solution contains 2.8% citric acid with the final pH 3.9. A 10% hemiacidrin solution contains 5.6% citric acid with pH 3.6, close to the commerically available Renacidin ® formulation.

This invention provides for a chemolytic solution for irrigation and in vivo dissolution of kidney stones, particularly struvite kidney stones. The solution exhibits stone dissolution characteristics far superior to those chemolytic solutions presently available. It has been found that by controlling citric concentration, and pH, and by use of pharmacologically acceptable chelating agents above specified threshold concentrations provides a superior formulation for in vivo calculi chemolysis.

It is therefore one object of this invention to provide an improved composition for in vivo dissolution of struvite calculi.

It is another object of this invention to provide an improved method for treatment of kidney stones utilizing a novel renal irrigant.

It is still another object of this invention to provide a novel chemolytic agent which can be used effectively alone or in combination with extracorporeal shock wave lithotripsy or percutaneous nephrostolithotomy.

BRIEF DESCRIPTION OF THE DRAWING

FIG. 1 is a graphical representation of the rates of dissolution of struvite stones with various chemolytic solutions.

DETAILED DESCRIPTION OF THE INVENTION

The present invention is directed to a chemolytic composition for dissolution of struvite calculi (kidney stones). The composition comprises about 5 to about 20% by weight citric acid or a pharmacologically acceptable salt thereof, and a pharmacologically acceptable chelating agent at a concentration sufficient to enhance stone dissolution. The composition is formulated as a sterile aqueous solution at a pH between about 3 and about 4.5.

Exemplary of suitable chelating agents include ethylenediaminetetraacetic acid (EDTA), N-(hydroxyethyl)ethylenetriaminetetraacetic acid, and nitrilotriacetic acid. A preferred chelating agent for use in accordance with the present invention is ethylenediaminetetraacetic acid, and its pharmacologically acceptable salts.

When EDTA is used as a chelating agent, it should be employed in the present composition at a level sufficient to give the prepared irrigating solution an EDTA concentration greater than about 0.01 M, preferably about 0.05 M to about 0.2 M.

Citric acid is used in the present formulation to form about 5 to about 20% by weight of the chemolytic solution. Preferably citric acid is used at a level of about 8 to about 15%, more preferably about 10 to about 12% by weight of the chemolytic solution.

Solution pH can range from about 3 to about 4.5 with a pH range of about 3.5 to about 4 being preferred. While pH can be adjusted using any pharmacologically acceptable base or buffering agent, sodium hydroxide is most preferred.

The components of the present chemolytic composition can be combined in the dry state in the appropriate weight ratios for addition to sterile water in accordance with a predetermined formula. In a preferred embodiment of the present invention a solution for dissolving struvite kidney stones is prepared by combining 2.5 g of ethylenediaminetetraacetic acid, 12 g of citric acid and 31 cc of 5 M sodium hydroxide and diluting the resulting mixture to a final volume of 100 cc. The solution can be administered to a patient using art-recognized renal irrigation techniques. The progress of stone dissolution can be monitored fluoroscopically.

The rate of kidney stone dissolution is enhanced by coincident extracorporeal shock wave lithotripsy or percutaneous nephrostolithotomy. The combined therapy has been shown to be uniquely effectively for the non-invasive removal of kidney stones.

Experimental Methods and Materials

A laboratory ultrasound device was used to facilitate study of the effect of the present chemolytic compositions on human struvite kidney stones. The ultrasonic transducer was driven by an amplified calibrated radiofrequency source. Multiple frequencies and amplitudes were investigated to find optimal parameters and all experiments presented were conducted at the same fixed energy output at the focal point, as calibrated by a steel ball deflexion device.

Human kidney stones were obtained from the Institute for Kidney Stone Research Indianapolis and Beck Analytical Laboratories. Stone composition was determined by Beck Laboratories and stones varied from 60% to 100% in total struvite composition. Stone size ranged from 200 to 1500 milligrams. Small fragments obtained from the ultrasound lithotrite were also studied. Stones were placed in a latex finger cot containing 7.0 cc of chemolytic agent at various concentrations and pH. The stone was then fixed a the focal point of the ultrasound beam. The transducer and stone were submerged together in a 37° C. degassed water bath. A corresponding matched control stone was also placed in a finger cot with 7 cc of chemolytic solution and located in the water bath outside the ultrasound field. Absolute weight loss of both control and experimental stones were assessed to 0.001 gram at various times before total dissolution. The control stone was then subsequently used as the experimental stone in the following experiment. All chemicals were reagent grade and obtained from Sigma Chemical except hemiacidrin which was obtained from Guardian Chemical Company, as Renacidin ®. Solutions were prepared fresh daily using degassed water. Ethylene diamine tetraacetic acid (EDTA) was used in anhydrous form. Rate of stone chemolysis was graphically represented by applying either absolute mass loss of stone in grams versus elapsed ultrasound time or as a percent of initial stone weight. Chemolysis was measured at a fixed elapsed ultrasound time of 24 minutes. Two-sample T-tests were preformed for data comparison and significance was established at $p < 0.01$. Data points were represented as the mean values ± the standard error of the means (SEM).

Results

Initial experiments were conducted to determine if acceleration of chemolysis by application of ultrasound would occur. Average stone size was 570 mg. Following 24 minutes of ultrasound time, experimental stones (N=9) lost 39 mg.+11 mg. (7% of its original weight), while control stones lost an average 0.5 mg., for a 75 fold increase in dissolution rate.

Observed variability in date suggested a surface area effect and further investigation using both single stones and multiple small fragments (to maximize surface area) demonstrate a linear relationship between absolute weight loss and stone size. Therefore, to account for variability secondary to surface area, data was represented as percent of initial stone size, which uniformly decreased the SEM. To understand the mechanism of hemiacidrin action on struvite stones, dissolution was first measured as a function of hemiacidrin concentration. Concentrations from 2.5% to 15% were studied since concentrations within this range are routinely used clinically following percutaneous stone procedures for irrigation of the remaining small fragments. A linear increase in stone dissolution with increase in hemiacidrin concentration was found. The dissolution rate at 10% hemiacidrin was three times that at 5%. This threefold increase in activity could be explained either by a pH effect, an increase in concentration of the components of the solution, or both. An inverse relationship exists between solution concentration and pH. A 5% hemiacidrin solution contains 2.8% citric acid with final pH 3.9. A 10% hemiacidrin solution contains 5.6% citric acid with pH 3.6. The pH versus concentration effect was further investigated by measuring dissolution at fixed pH while varying hemiacidrin concentration. Dissolution of struvite calculi was demonstrated to be profoundly sensitive to pH, but also dependent on concentration, but to a lesser extent.

The pH ranges from 2.0 to 3.5 and 4.5 to 7.5 at 0.5 increments were also examined. At pH $>4.0$, the dissolution activity of hemiacidrin decreases with no significant dissolution above control values at pH $>4.5$. There was exponential increase in dissolution rate from 3.6 to 2.0 with a peak dissolution rate of 70% +9% (24 minute ultrasound) at pH 2.0 This dissolution rate was independent of hemiacidrin concentration. Despite this high dissolution rate, however, it remains of theoretical interest only since the caustic effect to urothelium would preclude any clinical applicability at pH $<3.5$.

The role of citrate within the hemiacidrin solution was studied. Citric acid appears to have intrinsic dissolution properties independent of the simple liberation of hydrogen ion and subsequent neutralization of the ammonium component of the struvite stone. To further investigate this effect, we controlled pH at 3.6, 3.9, and 4.0 and at each pH varied citric concentration from 5 to 20%. The solutions were buffered using sodium carbonate and calcium carbonate initially, as historically these were used by Suby and Mulvaney [Suby, H.I. and Albright, F.: Dissolution of Phosphatic Urinary Calculi by the Retrograde Induction of Citrate Solution Containing Magnesium, *New Engl. J. Med.*, 228: 81, 1943; Mulvaney, W. P., A new solvent For Certain Urinary Calculi: A Preliminary Report, J. Urol., 82: 546, 1959]. However, these buffers were inadequate in that liberation of $CO_2$ during mixing made a degassed state impossible for the solvent, thereby interfering with ultrasound delivery ($CO_2$ being a poor sound wave medium). Moreover, carbonate compounds are difficult to dissolve and accurately titrate. We therefore used 5.0 M sodium hydroxide. Control studies demonstrated a small (2%) but statistically significant increase in dissolution rate with this buffer, probably secondary to improved sound transmission and decreased competitive inhibition by calcium for citric acid.

A linear increase in ultrasound mediate solution with increase in citric concentration was found at all pH's studied. The peak dissolution activity is at approximately 12% citric acid. Above this concentration there is slight increase in activity, however, the difficult in buffering becomes significant. At pH 3.9, 12% citrate demonstrates a dissolution rate of 31% as compared to a 4% dissolution rate for hemiacidrin at pH 3.9. This eightfold increase in dissolution rate at 3.9 is indicative of the intrinsic ability of citric acid to stimulate stone dissolution.

The drawing illustrates the relative rates of struvite stone dissolution in the presence of incident ultrasound radiation. The composition of the respective chemolytic solutions are as follows: 1, 5% Renacidin ® (pH 3.9); 2, 10% Renacidin ® (pH 3.6); 3, 12% citrate (pH 3.9); 4, 12% citrate (pH 3.6); 5, 12% citrate plus 0.1 M EDTA (pH 3.9); 6, 12% citrate plus D-gluconic acid (pH 3.9); 7, 12% citrate plus 0.1 M EDTA plus MgO (pH 3.9) [n=5, Mean+SEM].

D-glutamic acid is also described as an active dissolution agent for struvite stone, and its effect was therefore investigated. When 1.5% D-glutamic acid was added to 4% citrate buffer at pH 3.9, there was no significant increase in dissolution activity. At 5% citrate concentration, D-glutamic acid did potentiate chemolysis by 2%.

Several authors have suggested that EDTA could potentiate calcium stone dissolution by chelating the calcium component. [Dretler, S. P. and Pfister, R. C.: Primary Dissolution Therapy of Struvite Calculi, *J. urol.*, 131:861, 1984.] Since EDTA is also known to form chelates with magnesium, the effect of EDTA addition to the 12% citrate buffer was examined. Various EDTA concentrations were examined, however, only at concentrations greater than about 0.05 molar EDTA was stone dissolution potentiated. At about 0.10 molar EDTA we noted an increase in dissolution rate to 38% at pH 3.9 (24 minutes elapsed sound time).

Magnesium oxide has also been used as a component of chemolytic solutions. We therefore added magnesium ion in concentration similar to that used in hemiacidrin to 12% citrate buffer with and without EDTA. In both cases it significantly decreased the dissolution rate to 25% and 27% respectively. See the illustration in the drawing.

To determine if citrate buffer plus EDTA (CBE) would have increased activity over hemiacidrin in the absence of ultrasound potentiation, stones ranging in weight from 1.70 gm. to 0.59 gm. were placed in a latex finger cot containing CBE and softly agitated in a 37° C. water bath for 2 hours to 24 hours. Average weight loss for 24 hours was 0.729+0.084 gm. in CBE and 0.091 gm. ±0.018 gm. in hemiacidrin. There was linear increase in weight loss over 24 hours for both solutions. At each two hour time interval there was approximately an eightfold increase in CBE activity over hemiacidrin. Considering struvite density to be approximately 0.250 gm./cm$^3$, this would corresponds roughly to dissolution of a 2 cm$^3$ stone in 24 hours.

Struvite renal calculi represent a difficult therapeutic challenge, and some patients undergoing PCNL or ESWL procedures will have retained stone fragments which may well lead to new stone growth. To help clear the upper urinary tract of these potentially troublesome fragments, there has been renewed interest in chemolysis. However, there remains only limited date concerning mechanism of struvite chemolysis and only a few new chemolytic agents have been proposed over the past 20 years.

The data reported above demonstrates the action of hemiacidrin is dependent both on the pH of the solution and the absolute citrate concentration. Further, the action of EDTA can enhance the chemolytic activity of citric acid buffer above defined threshold EDTA concentrations.

It is not surprising that magnesium oxide decreases the activity of the buffer since it actively competes for ionic binding sites on the EDTA and citrate molecules. The addition of magnesium-based compounds for dissolution (such as magnesium carbonate in hemiacidrin) seams contradictory since during dissolution there is probable supersaturation of the solution with magnesium ion from intrinsic breakdown of the struvite crystal. Adding magnesium ion to the dissolution agent would thus increase competitive inhibition and decrease buffer activity, a concept support by the above data. The presence of magnesium has been responsible for significant toxicity due to excessive absorption during irrigation.

A preferred buffer for the dissolution of struvite calculi is 12% citric acid with 0.10 molar EDTA, pH titrated to 3.9 with 5 molar sodium hydroxide and free of added magnesium. While a solution with pH 3.6 would have significantly greater acitivity, the urothelium is exquisitely sensitive to low pH in this range and although 10% hemiacidrin's pH is 3.6, it is likely a solution at pH 3.9 would be clinically better tolerated.

Approaching the importance of the chemolytic buffer of this invention is the basic ultrasound technology presented. The use of ultrasound allows rapid investigation of dissolution by potentiating chemolysis, probably through a microcavitation process. Significant dissolution can be achieved in minuted, rather than hours or days, thereby allowing for rapid screening comparsion of chemolytic agents and of subtle changes in solution composition. Data showing that a compound developed using ultrasound will subsequently work without ultrasound potentiation has also been obtained. This technology could easily be used to study chemolytic agents for other stone types such as cystine, uric acid and calcium oxalate. Finally, the possibility for clinical use in vivo of broad beam ultrasound to potentiate chemolysis is being investigated, as it may represent a valuable adjunct to PCNL and ESWL, or a new area of primary therapy in high risk patients.

I claim:

1. A chemolytic composition for in vivo dissolution of calculi comprising
    about 5 to about 20% citric acid or a pharmacologically acceptable salt thereof; and
    a chelating agent selected from the group consisting of ethylenediaminetetraacetic acid, N-(hydroxyethyl)ethylenediaminetriacetic acid and nitrilotriacetic acid at a concentration of at least about 0.05 M, in a sterile aqueous medium at a pH between about 3 and about 4.5.

2. The chemolytic composition of claim 1 containing about 10 to about 15% citric acid.

3. The chemolytic composition of claim 2 wherein the chelating agent is ethylenediaminetetraacetic acid.

4. The chemolytic composition of claim 3 wherein the pH is adjusted to between about 3.5 and about 4.

5. A method of dissolving struvite kidney stones comprising contact said stones with a chemolytic composition in accordance with claim 4.

6. The method in accordance with claim 5 wherein the kidney stones are contacted with said compositions in the presence of incident ultrasound.

7. A method of dissolving struvite kidney stones comprising contacting said stones with a chemolytic composition with accordance with claim 3.

8. The method of claim 7 wherein the kidney stones are contacted with said composition in the presence of incident ultrasound.

9. A method of dissolving calculi (kidney stones) comprising contacting said stone with a chemolytic composition in accordance with claim 1.

10. The method of claim 9 wherein the kidney stones are contacted with said composition in the presence of incident ultrasound.

11. In a chemolytic stern aqueous solution adapted for dissolution of struvite kidney stones and containing citric acid, the improvement which comprises adjusting the concentration of said citric acid to about 10 to about 15% by weight of said solution and adding the chelating agent ethylenediaminetetraacetic acid to a concentration of about 0.05 to about 0.20 M, said solution having a pH between 3 and 4.5.

12. The improvement of claim 11 wherein the pH of the solution is adjusted to between about 3.5 and about 4.0.

13. The improvement of claim 12 wherein the citric acid concentration is about 12% by weight, and the EDTA concentration is about 0.1 M.

* * * * *